US006242591B1

(12) United States Patent
Cole et al.

(10) Patent No.: US 6,242,591 B1
(45) Date of Patent: Jun. 5, 2001

(54) SYNTHESIS OF SULFURIZED 2'-SUBSTITUTED OLIGONUCLEOTIDES

(75) Inventors: Douglas L. Cole, San Diego; Vasulinga T. Ravikumar, Carlsbad; Zacharia S. Cheruvallath, San Diego, all of CA (US)

(73) Assignee: Isis Pharmaceuticals, Inc., Carlsbad, CA (US)

( * ) Notice: Subject to any disclaimer, the term of this patent is extended or adjusted under 35 U.S.C. 154(b) by 0 days.

(21) Appl. No.: 09/481,486

(22) Filed: Jan. 11, 2000

Related U.S. Application Data

(63) Continuation-in-part of application No. 08/950,779, filed on Oct. 15, 1997, now Pat. No. 6,114,519.

(51) Int. Cl.$^7$ .................................................. C07H 21/00
(52) U.S. Cl. .................. 536/25.3; 536/25.33; 536/25.34; 568/22
(58) Field of Search ............................... 536/25.3, 25.33, 536/25.34; 568/22

(56) References Cited

U.S. PATENT DOCUMENTS

| 3,923,763 | * | 12/1975 | Edmondson | 526/217 |
| 4,245,033 | | 1/1981 | Eida et al. | 430/353 |
| 5,264,566 | * | 11/1993 | Froehler et al. | 536/25.34 |
| 5,902,881 | * | 5/1999 | Cheruvallath et al. | 536/25.3 |
| 6,114,519 | * | 9/2000 | Cole et al. | 536/25.34 |

FOREIGN PATENT DOCUMENTS

| 8902521 | | 10/1989 | (NL) . |
| 9116331 | * | 10/1991 | (WO) . |
| 9609406 | * | 3/1996 | (WO) . |

OTHER PUBLICATIONS

Zhang et al.(I), "Synthesis and Properties of Novel Thiono Triester Modified Antisense Oligodeoxynucleotide Phosphorothioates," *Bioorganic & Medicinal Chem. Letters*, 5(15), 1735–1740 (Aug. 3, 1995).*
Zhang et al, (II), "Thiono Triester Modified Antisense Oligonucleotides for Inhibition of Human Cytomegalovirus In Vitro," *Bioorganic & Medicinal Chem. Letters*, 6(16), 1911–1916 (Aug. 20, 1996).*
Bokarev et al., "Synthesis of Bis(Alkyl Xanthyl) Trisulfides," *Izv. Akad. Nauk SSSR. Ser. Khim.*, 1964(12), 2175–2182; *Chem. Abstr.*, 62(7), Abstr. No. 7631d (Mar. 29, 1965); only Abstract supplied.*
Scholl et al., "Novel Symmetrical and Mixed Carbamoyl and Amino Polysulfanes by Reactions of (Alkoxydichloromethyl)polysulfuranyl Substrates with N–Methylaniline," *J. Organic Chem.*, 51(10), 1866–1881 (1986).*
Barany et al., "A General Strategy for Elaboration of the Dithiocarbonyl Functionality, –(C=O)SS–: Application to the Synthesis of Bis(chlorocarbonyl)disulfane and Related Derivatives of Thiocarbonic Acids," *J. Organic Chem.*, 48(24), 4750–4761 (Dec. 2, 1983).*

Carey et al., *Advanced Organic Chemistry, 3rd Ed., Part A: Structure and Mechanisms*, Plenum Press, New York, NY, 1990, only pp. 473–475 supplied.*
DeBont et al., "Solid–phase synthesis of O–phosphorothioylserine–and–threonine–containing peptides as well as O–phosphoserine–and–threonine–containing peptides", *J. Org. Chem.*, 1993, 58(6), 1309–1317.
Dreef, C.E. et al., "An expeditious synthesis of biologically important myo–inositol phosphorothioates", *Bioorg. Med. Chem. Lett.*, 1991, 1(5), 239–242.
Iyer, R., Beaucage, Serge L. et al., "3H–1, 2–benzodithiole–3–one 1,1–dioxide as an improved sulfurizing reagent in the solid–phase synthesis of oligodeoxyribonucleoside phosphorothiioates", *J. Am. Chem. Soc.*, 1990, 112, 1253–1255.
Iyer, R.P. et al., "The Automated Synthesis of Sulfur–Containing Oligodeoxyribonucleotides Using 3H–1, 2–Benzodithiol–3–one 1,1,–Dioxide as a Sulfur–Transfer Reagent", *J. Org. Chem.*, 1990, 55(15), 4693–4699.
Kamer et al., "An Efficient Approach Toward the Synthesis of Phosphorothioate Diesters Via the Schönberg Reaction", *Tetra. Lett.*, 1989, 30(48), 6757–6760.
Kodomari et al., "A Convenient Synthesis of Bis[acyl] Disulfides using Phase–Transfer Catalysis", *Synthesis*, 1981, 637–638.
Kozikowski, A.P. et al., "Tools for Cell Signaling: Synthesis of the 3–Phosphatase–Resistant 1,3,4,5–InsP4 Mimic, ID–myo–Inositol 1,4,5–Trisphosphate 3–Phosphorothioate", *J. Org. Chem.*, 1994, 59(9), 2279–2281.
Lozano, J.I. et al., "Electrosynthesis of 2–benzhydrylidene–4,4–diphenyl–1, 3–oxathiolan–5–one: the reaction pathway", *Tetrahedron*, 1996, 52(4), 1259–1266.
Roelen et al., "A study on the use of phenylacetyl disulfide in the solid–phase synthesis of oligodeoxynucleoside phosphorothioates", *Rech. Trav. Chim. Pays–Bas*, 1991, 110, 325–331.
Wyrzykiewicz, T.K. et al., "Efficiency of sulfurization in the synthesis of oligodeoxyribonucleotide phosphorothioates utilizing various sulfurizing reagents", *Bioorg. Med. Chem. Lett.*, 1994, 4(12), 1519–1522.

* cited by examiner

*Primary Examiner*—Gary Geist
*Assistant Examiner*—L. E. Crane
(74) *Attorney, Agent, or Firm*—Woodcock Washburn Kurtz Mackiewicz & Norris LLP

(57) ABSTRACT

Methods for the formation of sulfurized oligonucleotides are provided. The methods allow for the formation of phosphorothioate linkages in the oligonucleotides or derivatives, without the need for complex solvent mixtures and repeated washing or solvent changes. Oligonucleotides having from about 8, and up to about 50, nucleotides can be sulfuiized according to the methods of the invention with higher yields than have been previously reported.

19 Claims, No Drawings

SYNTHESIS OF SULFURIZED 2'-SUBSTITUTED OLIGONUCLEOTIDES

This application is a continuation-in-part of U.S. application Ser. No. 08/950,779, filed on Oct. 15 1997, now U.S. Pat. No. 6,114,519.

FIELD OF THE INVENTION

The present invention is directed to methods for synthesizing sulfurized oligonucleotides and analogs thereof The methods employ a phenylacetyl disulfide reagent in a simplified solvent system and produce oligonucleotides having phosphorothioate groups with great efficiency and improved yields.

BACKGROUND OF THE INVENTION

Modified oligonucleotides are of great value in molecular biological research and in applications such as anti-viral therapy. Modified oligonucleotides which can block RNA translation, and are nuclease resistant, are useful as antisense reagents. Sulfurized oligonucleotides, which contain phosphorothioate (P-S) linkages, are of interestin these areas. Phosphoiothioate-containing oligonucleotides are also useful in determining the stereochemical pathways of certain enzymes which recognize nucleic acids.

Standard techniques for sulfurization of phosphorous-containing compounds have been applied to the synthesis of sulfurized oligonucleotides. Examples of sulfurization reagents which have been used to synthesize oligonucleotides containing phosphorothioate bonds include elemental sulfur, dibenzoyltetrasulfide, 3-H-1,2-benzidithiol-3-one 1,1-dioxide (also known as Beaucage reagent), tetraethylthiuram disulfide (TETD), and bis(O,O-diisopropoxy phosphinothioyl) disulfide (known as Stec reagent). Most of the known sulfurization reagents, however, have one or more significant disadvantages.

Elemental sulfur presents problems and is not suitable for automation because of its insolubility in most organic solvents. Furthermore, carbon disulfide, a preferred source of sulfur, has undesirable volatility and an undesirably low flash point. Unwanted side products are often observed with the use of dibenzoyl tetrasulfide. Beaucage reagent, while a relatively efficient sulfurization reagent, is difficult to synthesize and not particularly stable. Furthermore, use of Beaucage reagent forms a secondary reaction product which is a potent oxidizing agent. (R. P. Iyer et al., *J. Am. Chem. Soc*112, pp. 1253–1254 (1990); R. P. Iyer et al., *J. Org. Chem.* 55, 4693–4699 (1990)). This can further lead to unwanted side products which can be difficult to separate from the desired reaction product. Tetraethylthiuram disulfide, while relatively inexpensive and stable, has a sulfurization reaction rate which can be undesirable slow.

A method for producing a phosphorothioate ester by reaction of a phosphite ester with an acyl disulfide is disclosed in Dutch patent application No. 8902521. The disclosed method is applied to a purified phosphotriester dimer utilizing solution phase chemistry. The method is time and labor intensive in that it was only shown to work in a complex scheme which involved carrying out the first stage of synthesis (formation of a phosphite) in acetonitrile, removing the acetonitrile, purifying the intermediate phosphotriester, and proceeding with the sulfurization in a solvent mixture of dichloroethane (DCE) and 2,4,6-collidine. Furthermore, the method was demonstrated only with a dinucleotide. There was no suggestion that the Dutch method could be employed with larger nucleic acid structures, that the same could employ a common solvent throughout all steps of synthesis, that improved yields could be obtained, or that the method could be adapted for conventional automated synthesis without extensive modification of the scheme of automation. Although acetonitrile is mentioned as one of several possible solvents, utility of the method for carrying out all steps of the synthesis in acetonitrile as a common solvent was not demonstrated. While other publications (Kamer et al., Tetrahedron Letters 30(48), pp. 6757–6760 (1989); Roelen etal., Rech. Trav. Chim. Pays-Bas 110, pp.325–331 (1991)) show sulfurization of oligomers having up to 6 nucleotides, the foregoing shortcomings are not overcome by the methods disclosed in these references.

Thus, there remains a need for improved methods and reagents for preparing sulfur-containing phosphorous groups, such as phosphorothioate linkages, in oligonucleotides and other organic compounds. The present invention is directed to these, as well as other, important ends.

SUMMARY OF THE INVENTION

The present invention provides methods for synthesis of phosphorothioate oligonucleotides with improved yields as compared to those obtained with prior methods. Moreover, the present methods are useful for the synthesis of not only phosphorothioate oligonucleotides having relatively large numbers of nucleotide and/or nucleoside units therein, e.g. from about 6 to about 50, and even more, and particularly from about 8 to about 30 nucleotide and/or nucleoside units. The methods of the present invention employ a greatly simplified solvent system, one which is compatible with automated synthetic reaction schemes and commercial synthesizers. The resulting improvement in synthetic opportunities permits wide application of the present methods throughout nucleic acid chemistry.

One aspect of the present invention discloses methods for synthesizing phosphorothioate oligonucleotides, comprising the steps of phosphitylating a 5'-hydroxyl moiety of a nucleotide, nucleoside, oligonucleotide or an oligonucleoside, and contacting the resultant phosphite intermediate with a phenylacetyl disulfide in the presence of a solvent system that includes acetonitrile for a time sufficient to effect the formation of a phosphorothioate functional group. Phosphorothioate oligonucleotides having a predetermined length and sequence can be prepared by repeating the phosphitylating and oxidizing steps.

In further aspects of the present invention, methods for the synthesis of phosphorothioate oligonucleotide analogs are disclosed, comprising the substitution of modified nucleotides, nucleosides, oligonucleotides and oligonucleosides for nucleotides, nucleosides, oligonucleotides or oligonucleosides. Modifications to nucleotides, nucleosides, oligonucleotides and oligonucleosides are well known in the art. As used herein the term "phosphorothioate oligonucleotide" is meant to include analogs as defined above.

The term "phosphite moiety" as used herein is meant to include phosphite moieties within nucleosides, nucleotides, oligonucleosides and oligonucleotides. In a preferred embodiment, phosphite moieties are in an activated state such as a dimethoxytritylphosphoramidite. The terms "nucleotide, nucleoside, oligonucleotide or an oligonucleoside" as used herein are intended to include both naturally occurring species and non-naturally occurring or modified species as is known to those skilled in the art. Common modifications include sugar modifications such as 2' modifications and base modifications or the use of substitute bases. When an oligonucleotide or modified oligonucleotide is used as the phosphite moiety, modified linkages as is commonly known in the art may also be present.

The present methods have demonstrated lower levels of impurities and higher yields compared to when DCE is used as a solvent for the oxidation step. The present methods have also shown, unexpectedly, that yields of about 99% can be obtained in acetonitrile/picoline. Acetonitrile/picoline is entirely compatible with automated synthesis without extensive modification to the synthetic routine, so that the present methods can be advantageously used in an automated synthesizer. For example, extensive washes are not required because a single solvent or mixture having a common solvent is used in all automated synthetic steps. Thus, solvent removal and wash steps can be eliminated. It has also been surprisingly discovered that high yields can be achieved when synthesizing phosphorothioate oligonucleotides or oligonucleotide analogs having from about 8 nucleotides and up to about 30 nucleotides.

Suitable solvent systems for use in the oxidation of the phosphite intermediate of the present invention include mixtures of two or more solvents. Preferably a mixture of an aprotic solvent with a protic or basic solvent. Preferred solvent mixtures include acetonitrile/picoline and acetonitrile/lutidine. Suitable aprotic solvents include pyridine and hindered pyridines such as lutidine, collidine, and picoline. Solvent mixtures can include, for example, two solvents such as acetonitrile and picoline, or acetonitrile and lutidine, in a volume ratio of from about 1:1.5 to about 1.5:1, preferably about 1:1.

Sulfurization (oxidation utilizing a sulfurizing reagent), according to the methods of the present invention, is carried out by contacting an oligonucleotide or analog with an acetyl disulfide for a time sufficient to effect formation of a phosphorothioate functional group. Preferred reagents include phenylacetyl disulfide, arylacetyl disulfide, and aryl substituted phenylacetyl disulfides.

Contacting the phosphite moiety with acetyl disulfide can be done using procedures and equipment known to those skilled in the art. For example, a glass reactor such as a flask can be suitably employed. Preferably, solid phase synthesis procedures are employed, and a solid support such as controlled pore glass. Even more preferably, the methods of the present invention can be carried out using automatic DNA synthesizers. Suitable solid phase techniques, including automated synthesis techniques, are described in F. Eckstein (ed.), *Oligonucleotides and Analogues, a Practical Approach*, Oxford University Press, New York (1991).

The methods of the present invention can be suitably carried out at room temperature. "Room temperature" includes ambient temperatures from about 20° C. to about 30° C. Reaction times are on the order of minutes, such as, for example, 2, 3, 4, or 5 minutes, or even as short as about 100 seconds.

Generally, methods of the present invention include phosphitylating the 5'-hydroxyl group of a nucleic acid moiety to form a phosphite intermediate and oxidizing the phosphite intermediate with an acetyl disulfide for a time sufficient to effect conversion of the phosphite intermediate to a phosphorothioate. The phosphite intermediate can be, for example, a phosphite linked dinucleotide, or an oligonucleotide or oligonucleoside having at least one phosphite linkage therein. The phosphitylation and oxidation steps of the method are both performed in a system that includes acetonitrile. Repetition of the phosphitylation and oxidation steps will give the phosphorothioate oligonucleotide having a predetermined length. Reaction progress can be monitored by well-known techniques such as proton or $^{31}$P NMR. The reaction product can be treated with a base such as, for example, ammonium hydroxide solution at a concentration of about 30 percent. The desired product can be readily isolated by, for example, standard filtration techniques.

The following examples are merely illustrative of the present invention and should not be considered limiting of the scope of the invention in any way. These examples and equivalents thereof will become more apparent to those skilled in the all in light of the present disclosure and the accompanying claims.

EXAMPLE 1

Synthesis of 5'-TTTTTTT-3' phosphorothioate heptamer:

50 milligram (2 μmole) of 5'-O-dimethoxytritylthymidine bound to CPG (controlled pore glass) through an ester linkage is taken up in a glass reactor, and a dichloromethane solution of 2% dichloroacetic acid (volume/volume) is added to deprotect the 5' hydroxyl group. The product is washed with acetonituile. Then, a 0.2 M solution of 5'-O-(4,4'-dimethoxytrityl)thymidine-3'-O-(2-cyanoethyl N,N-diisopropylphosphoramidite) in acetonitrile and a 0.4 M solution of 1H-tetrazole in acetonitrile is added, and allowed to react at room temperature for 5 minutes. The product is washed with acetonitrile, and then a 0.2 M solution of phenylacetyl disulfide in acetonitrile:3-picoline (1:1 v/v) is added and allowed to react at room temperature for 3 minutes. This sulfurization step is repeated one more time for 3 minutes. The support is washed with acetonitrile, and then a solution of acetic anhydride/lutidine/THF (1:1:8), and N-methyl imidazole/THF is added to cap any unreacted 5'-hydroxyl group. The product is washed with acetonitrile.

This complete cycle is repeated five more times to produce the completely protected thymidine heptamer. The carrier containing the compound is treated with 30% aqueous ammonium hydroxide solution for 90 minutes at room temperature. The aqueous solution is filtered, and concentrated under reduced pressure to give a phosphorothioate heptamer, TTTTTTT.

EXAMPLE 2

Synthesis of 5'-d(GACT)-3'phosphorothioate tetramer:

50 milligram ($2 \times 10^{-6}$ mole (2 μmole)) of 5'-O-dimethoxytritylthymidine bound to CPG (controlled pore glass) through an ester linkage is taken up in a glass reactor, and a dichloromethane solution of 2% dichloroacetic acid (volume/volume) is added to deprotect the 5'-hydroxyl group. The product is washed with acetonitiile. Then, a 0.2 M solution of 5'-O-(4,4'-dimethoxytrityl)thymidine-3'-O-(2-cyanoethyl N,N-diisopropylphosphoramidite) in acetonitrile and a 0.4 M solution of 1H-tetrazole in acetonitrile is added, and allowed to react at room temperature for 5 minutes. The product is washed with acetonitrile, and then a 0.2 M solution of phenylacetyl disulfide in acetonitrile:3-picoline (1:1 v/v) is added and allowed to react at room temperature for 3 minutes. This sulfurization step is repeated one more time for 3 minutes. The support is washed with acetonitrile and then a solution of acetic anhydride/lutidine/THF (1:1:8), and N-methyl imidazole/THF is added to cap the unreacted 5'-hydroxyl group. The product is washed with acetonitrile.

A solution of 2% dichloroacetic acid (volume/volume) is added to deprotect the 5'-hydroxyl group The product is washed with acetonitrile. Then, a 0.2 M solution of $N^4$-benzoyl-5'-O-(4,4' dimethoxytrityl)-2'-deoxycytidine-3'-O-(2-cyanoethyl N,N'diisopropyl phosphoramidite) in acetonitrile and a 0.4 M solution of 1H-tetrazole in acetonitrile is added, and allowed to react at room temperature for 5 minutes. The product is washed with acetonitrile, and then a 0.2 M solution of phenylacetyl disulfide in acetonitrile:3 picoline (1:1 v/v) is added and allowed to react at room temperature for 3 minutes. This sulfurization step is repeated one more time for 3 minutes. The support is washed with acetonitrile and then a solution of acetic anhydride/lutidine/THF (1:1:8), and N-methyl imidazole/THF is added to cap any unreacted 5'-hydroxyl group. The product is washed with acetonitrile.

A solution of 2% dichloroacetic acid (volume/volume) is added to deprotect the 5'-hydroxyl group. The product is washed with acetonitrile. Then, a 0.2 M solution of N6-benzoyl-5'-O-(4,4' dimethoxytrityl)-2'-deoxyadenosine-3'-O-(2-cyanoethyl-N,N'diisopropylphosphoramidite) in anhydrous acetonitrile and a 0.4 M solution of 1H-tetrazole in acetonitrile is added, and allowed to react at room temperature for 5 minutes. The product is washed with acetonitiile, and then a 0.2 M solution of phenylacetyl disulfide in acetonitrile:3-picoline (1:1 v/v) is added and allowed to react at room temperature for 3 minutes. This sulfurization step is repeated one more time for 3 minutes- The support is washed with acetonitrile and then a solution of acetic anhydride/lutidine/THF (1:1:8), and N-methyl imidazole/THF is added to cap the unreacted 5'-hydroxyl group. The product is washed with acetonitrile.

A solution of 2% dichloroacetic acid (volume/volume) is added to deprotect the 5'-hydroxyl group. The product is washed with acetonitrile. Then, a 0.2 M solution of N2-isobutyryl-5'-O-4,4'dimethoxytrityl-deoxyguanosine-3'-O-(2-cyanoethyl N,N'diisopropyl phosphoramidite) in acetonitrile and a 0.4 M solution of 1H-tetrazole in acetonitrile is added, and allowed to react at room temperature for 5 minutes. The product is washed with acetonitrile, and then a 0.2 M solution of phenylacetyl disulfide in acetonitrile: 3 picoline (1:1 v/v) is added and allowed to react at room temperature for 3 minutes. This sulfurization step is repeated one more time for 3 minutes. The support is washed with acetonitrile and then a solution of acetic anhydride/lutidine/THF (1:1:8), and N-methyl imidazole/THF is added to cap any unreacted 5'-hydroxyl group. The product is washed with acetonitrile.

The carrier containing the compound is treated with 30% aqueous ammonium hydroxide solution for 90 minutes at room temperature and then incubated at 55° C. for 24 hour. The aqueous solution is filtered, concentrated under reduced pressure to give a phosphorothioate tetramer of 5'-dG-dA-dC-T-3'.

EXAMPLE 3

Synthesis of fully-modified 5'-d(TCC-CGC-CTG-TGA-CAT-GCA-TT)-3' phosphorothioate 20-mer <Seq. ID No. 1>.

The synthesis of the above sequence was performed on a Pharmacia OligoPilot II Synthesizer on a 620 µmole scale using the cyanoethyl phosphoramidites and Pharmacia's primar support. Sulfulization was performed using a 0.2 M solution of phenylacetyl disulfide in aceonitrile:3-picoline (1:1 v/v) for 2 minutes. At the end of synthesis, the support was washed with acetonitrile, cleaved, deprotected and purified as has been previously illustrated above.

EXAMPLE 4

Synthesis of fully-modified 5'd(GCC-CAA-GCT-GGC-ATC-CGT-CA)3'phosphorothioate 20-mer <Seq. ID No. 2>.

The synthesis of the above sequence was performed on a Pharmacia OligoPilot II Synthesizer on a 620 µmole scale using the cyanoethyl phosphoramidites and Pharmacia's primar support. Sulfurization was performed using a 0.2 M solution of phenylacetyl disulfide in acetonitrile:3-picoline (1:1 v/v) for 2 minutes- At the end of synthesis, the support was washed with acetonitrile, cleaved, deprotected and purified as has been previously illustrated above.

EXAMPLE 5

Synthesis of fully-modified 5'-d(GCG-TTT-GCT-CTT-CTT-CTT-GCG)-3'phosphorothioate 21-mer <Seq. ID No. 3>.

The synthesis of the above sequence was performed on a Pharmacia OligoPilot II Synthesizer on a 620 µmole scale using the cyanoethyl phosphoramidites and Pharmacia's primar support. Sulfurization was performed using a 0.2 M solution ofphenylacetyl disulfide in aceonitrile:3-picoline (1:1 v/v) for 2 minutes. At the end of synthesis, the support was washed with acetonitrile, cleaved, deprotected and purified as has been previously illustrated above.

EXAMPLE 6

Synthesis of fully-modified 5'd(GTT-CTC-GCT-GGT-GAG-TTT-CA)-3' phosphorothioate 20-mer <Seq. ID No. 4>.

The synthesis of the above sequence was performed on a Pharmacia OligoPilot II Synthesizer on a 620 µmole scale using the cyanoethyl phosphoramidites and Pharmacia's primar support. Sulfurization was performed using a 0.2 M solution of phenylacetyl disulfide in aceonitrile:3-picoline (1:1 v/v) for 2 minutes. At the end of synthesis, the support was washed with acetonitrile, cleaved, deprotected and purified as has been previously illustrated above.

EXAMPLE 7

Synthesis of fully-modified 5'd(TCC-CGC-CTG;TGA)-2'-methoxyethyl-(CAU-GCA-UU)-3' phosphorothioate 20-mer <Seq. ID No. 5>.

The synthesis of the above sequence was performed on a Milligen 8800 Synthesizer on a 282 µmole scale using the cyanoethyl phosphoramidites and Pharmacia's primar support. Sulfurization was performed using a 0.4 M solution of phenylacetyl disulfide in acetonitrile:3-picoline (1:1 v/v) for 6 minutes. At the end of synthesis, the support was washed with acetonitrile, cleaved, deprotected and purified as has been previously illustrated above.

EXAMPLE 8

Synthesis of fully-modified 5' d(TCC-CGC-CTG-TGA) 2'methoxyethyl-(CAU-GCA-UU)3' phosphorothioate 20-mer <Seq. ID No. 6>.

The synthesis of the above sequence was performed on a Pharmacia OligoPilot II Synthesizer on a 250 µmole scale using the cyanoethyl phosphoramidites and Pharmacia's primar support. Sulfurization was performed using a 0.4 M solution of phenylacetyl disulfide in acetonitrile:3-picoline (1:1 v/v) for 10 minutes. At the end of synthesis, the support was washed with acetonitrile, cleaved, deprotected and purified as has been previously illustrated above.

EXAMPLE 9

Synthesis of fully-modified 5'-[2'-methoxyethyl (GCGUUUG)-d[CTCTTCT]-[2'-methoxyethyl-(UCUUGC)-dG-3' phosphorothioate 21-mer <Seq. ID No. 7>.

The synthesis of the above sequence was performed on a Pharmacia OligoPilot II Synthesizer on a 250 µmole scale using the cyanoethyl phosphoramidites and Pharmacia's primar support. Sulfurization was performed using a 0.4 M solution of phenylacetyl disulfide in aceonitrile:3-picoline (1-1 v/v) for 6 minutes. At the end of synthesis, the support was washed with acetonitrile, cleaved, deprotected and purified as has been previously illustrated above.

EXAMPLE 10
Synthesis of fully-modified 5'-d(GCC-CAA-GCT-GGC)-2'-methoxyethyl-(AUC-CGU-CA)-3' phosphorothioate 20-mer <Seq. ID No. 8>.

The synthesis of the above sequence was performed on a Milligen 8800 Synthesizer on a 565 µmole scale using the cyanoethyl phosphoramidites and Pharmacia's primar support. Sulfurization was performed using a 0.4 M solution of phenylacetyl disulfide in acetonitrile:3-picoline (1:1 v/v) for 6 minutes. At the end of synthesis, the support was washed with acetonitrile, cleaved, deprotected and purified as has been previously illustrated above.

EXAMPLE 11
Synthesis of fully-modified 5'-d(GCC-CAA-GCT-GGC)-2'-methoxyethyl-(AUC-CGU-CA)-3' phosphorothioate 20-mer <Seq. ID No. 9>.

The synthesis of the above sequence was performed on a Pharmacia OligoPilot II Synthesizer on a 680 µmole scale using the cyanoethyl phosphoramidites and Pharmacia's primar support. Sulfurization was performed using a 0.4 M solution of phenylacetyl disulfide in aceonitrile:3-picoline (1:1 v/v) for 6 minutes. At the end of synthesis, the support was washed with acetonitrile, cleaved, deprotected and purified as has been previously illustrated above.

EXAMPLE 12
Synthesis of fully-modified 5'-[2'-O-methoxyethyl-(TT-TTT-TTT-TTT-TTT-TTT-TT)-3' phosphorothioate 20-mer <Seq. ID No. 10>.

The synthesis of the above homo-pyrimidine sequence was performed on a Pharmacia OligoPilot II synthesizer on an 180 µmole scale using cyanoethyl phosphoramidite of 5'-O-DMT-2'-O-methoxyethyl-5-methyluridine. Pharmacia's HL 30 primer support loaded with 2'-O-methoxyethyl-5-methyluridine was used. Detritylation was performed using 3% dichloroacetic acid in toluene (volume/volume). Activation of phosphoramidite was done with a 0.45 M solution of 1H-tetrazole in acetonitrile. Sulfurization was performed using a 0.2 M solution of phenylacetyl disulfide in aceonitrile:3-picoline (1:1 v/v) for 2 minutes. At the end of synthesis, the support was treated with a solution of triethylamine: acetonitrile (1:1, v/v) for 12 hours, support washed with acetonitrile, oligo cleaved, and deprotected with 33% aqueous ammonium hydroxide at 55° C. for 12 hours, cooled, concentrated, and purified by reversed phase HPLC. All DMT fractions were combined, analyzed by capillary gel electrophoresis, detritylated, precipitated and lyophilized to a powder. The stepwise sulfurization efficiency was found to 99.6% based on $^{31}$P NMR (D$_2$O).

EXAMPLE 13
Synthesis of fully-modified 5'-[2'-O-methoxyethyl-(TTT-TTT-TTT-TTT-TTT-TTT-TT)-3' phosphorothioate 20-mer <Seq. ID No. 10>.

The synthesis of the above homo-pyrimidine sequence was performed on a Pharmacia OligoPilot II synthesizer on an 180 µmole scale using cyanoethyl phosphoramidite of 5'-O-DMT-2'-O-methoxyethyl-5-methyluridine. Pharmacia's HL 30 primer support loaded with 2'-O-methoxyethyl-5-methyluridine was used. Detritylation was performed using 3% dichloroacetic acid in toluene (volume/volume). Activation of phosphoramidite was done with a 0.22 M solution of pyridinium trifluoroacetate and 0.11 M solution of 1-methylimidazole. Sulfurization was performed using a 0.2 M solution of phenylacetyl disulfide in acetonitrile:3-picoline (1:1 v/v) for 2 minutes. At the end of synthesis, the support was treated with a solution of triethylamine:acetonitrile (1:1, v/v) for 12 hours, support washed with acetonitrile, oligo cleaved, and deprotected with 33% aqueous ammonium hydroxide at 55° C. for 12 hours, cooled, concentrated, and purified by reversed phase HPLC. All DMT fractions were combined, analyzed by capillary gel electrophoresis, detritylated, precipitated and lyophilized to a powder. The stepwise sulfurization efficiency was found to 99.7% based on $^{31}$P NMR (D$_2$O).

EXAMPLE 14
Synthesis of fully-modified 5'-[2'-O-methoxyethyl-(GCTGA]-d(TTA-GAG-AGA-G)-[2'-O-methoxyethyl-(GTCCC)-3' phosphorothioate 20-mer <Seq. ID No. 11>.

The synthesis of the above sequence was performed on a Pharmacia OligoPilot II synthesizer on an 180 µmole scale using cyanoethyl phosphoramidite of 2'-deoxyribonucleosides and 2'-O-methoxyethyl substituted ribonucleosides. Pharmacia's HL 30 primer support loaded with 2'-O-methoxyethyl-N4-benzoyl-5-methylcytidine was used. Detritylation was performed using 3% dichloroacetic acid in toluene (volume/volume). Activation of phosphoramidite was done with a 0.45 M solution of 1H-tetrazole in acetonitrile. Sulfurization was performed using a 0.2 M solution of phenylacetyl disulfide in acetonitrile:3-picoline (1:1 v/v) for 2 minutes. At the end of synthesis, the support was treated with a solution of triethylamine:aceonitrile (1:1, v/v) for 12 hours, support washed with aceonitrile, oligo cleaved, and deprotected with 33% aqueous ammonium hydroxide at 55° C. for 12 hours, cooled, concentrated, and purified by reversed phase HPLC. All DMT fractions were combined, analyzed by capillary gel electrophoresis, detritylayed, precipitated and lyophilized to a powder. The stepwise sulfurization efficiency was found to 99.7% based on $^{31}$P NMR (D$_2$O).

EXAMPLE 15
Synthesis of fully-modified 5'-[2'-O-methoxyethyl-(CTG]-d(AGT-CTG-TTT)-[2'-O-methoxyethyl-(TCC-ATT-CT)-3' phosphorothioate 20-mer <Seq. ID No. 12>.

The synthesis of the above sequence was performed on a Pharmacia OligoPilot II synthesizer on a 172 µmole scale using cyanoethyl phosphoramidite of 2'-deoxyribonucleosides and 2'-O-methoxyethyl substituted ribonucleosides. Pharmacia's HL 30 primer support loaded with 2'-O-methoxyethyl-5-methyluridine was used. Detritylation was performed using 3% dichloroacetic acid in toluene (volume/volume). Activation of phosphoramidite was done with a 0.45 M solution of 1H-tetrazole in acetonitrile. Sulfurization was performed using a 0.2 M solution of phenylacetyl disulfide in acetonitrile:3-picoline (1:1 v/v) for 2 minutes. At the end of synthesis, the support was treated with a solution of triethylamine:acetonitrile (1:1 v/v) for 12 hours, support washed with acetonitrile, oligo cleaved, and deprotected with 33% aqueous ammonium hydroxide at 55° C. for 12 hours, cooled, concentrated, and purified by reversed phase HPLC. All DMT fractions were combined, analyzed by capillary gel electrophoresis, detritylated, precipitated and lyophilized to a powder. The stepwise sulfurization efficiency was found to 99.7% based on $^{31}$P NMR (D$_2$O).

EXAMPLE 16
Synthesis of fully-modified 5'-[2'-O-methoxyethyl-(GCTGA]-d(TTA-GAG-AGA-G)-[2'-O-methoxyethyl-(GTCCC)-3' phosphorothioate 20-mer <Seq. ID No. 11>.

The synthesis of the above sequence was performed on a Pharmacia OligoProcess I Synthesizer on a 150 mmole scale using cyanoethyl phosphoramidite of 2'deoxyribonucleosides and 2'-O-methoxyethyl substituted ribonucleosides. Pharmacia's HL 30 primer support loaded with 2'-O-methoxyethyl-N4-benzoyl-5-methylcytidine was used. Detritylation was performed using 3% dichloroacetic acid in toluene (volume/volume). Activation of phosphoramidite was done with a 0.45 M solution of 1H-tetrazole in acetonitrile. Sulfurization was performed using a 0.2 M solution of phenylacetyl disulfide in acetonitrile:3-picoline (1:1 v/v) for 2.2 minutes. At the end of synthesis, the support was treated with a solution of triethylamine:acetonitrile (1:1, v/v) for 12 hours, support washed with acetonitrile, oligo cleaved, and deprotected with 33% aqueous ammonium hydroxide at 55° C. for 12 hours, cooled, concentrated, and purified by reversed phase HPLC. The DMT-on peak was fractionated, analyzed by capillary gel electrophoresis, combined, detritylated, precipitated and lyophilized to a powder. The stepwise sulfurization efficiency was found to 99.75% based on $^{31}$P NMR (D$_2$O).

EXAMPLE 17

Synthesis of fully-modified 5'-[2'-O-methoxyethyl-(CTG]-d (AGT-CTG-TTT)-[2'-O-methoxyethyl-(TCC-ATT-CT)-3' phosphorothioate 20-mer <Seq. ID No. 12>.

The synthesis of the above sequence was performed on a Pharmacia OligoPilot II synthesizer on a 40 mmole scale using cyanoethyl phosphoramidite of 2'-deoxyribonucleosides and 2'-O-methoxyethyl substituted ribonucleosides. Pharmacia's HL 30 primer support loaded with 2'-O-methoxyethyl-5-methyluridine was used. Detritylation was performed using 15% dichloroacetic acid in toluene (volume/volume). Activation of phosphoramidite was done with a 0.45 M solution of 1H-tetrazole in acetonitrile. Sulfurization was performed using a 0.2 M solution of phenylacetyl disulfide in acetonitrile:3-picoline (1:1 v/v) for 2.2 minutes. At the end of synthesis, the support was treated with a solution of triethylamine:aceonitrile (1:1, v/v) for 12 hours, support washed with acetonitrile, oligo cleaved, and deprotected with 33% aqueous ammonium hydroxide at 55° C. for 12 hours, cooled, concentrated, and purified by reversed phase HPLC. The DMT-on peak was fractionated, analyzed by capillary gel electrophoresis, combined, detritylated, precipitated and lyophilized to a powder. The stepwise sulfurization efficiency was found to 99.7% based on $^{31}$P NMR (D$_2$O).

EXAMPLE 18

Synthesis of fully modified 5'-d(TCC-CGC-CTG-TGA)-2'-O-methoxyethyl-(CAT-GCA-TT)-3' phosphorothioate 20-mer <Seq. ID No. 13>.

The synthesis of the above sequence was performed on a Milligen 8800 synthesizer on a 282 μmole scale using the cyanoethyl phosphoramidites and Pharmacia's HL 30 primer support. Detritylation was performed using 3% dichloroacetic acid in toluene (volume/volume). Sulfurization was performed using a 0.4 M solution of phenylacetyl disulfide in acetonitrile:3-picoline (1:1 v/v) for 4 minutes. At the end of synthesis, the support was treated with a solution of triethylamine:aceonitrile (1:1, v/v) for 12 hours, support washed with acetonitrile, oligo cleaved, and deprotected with 33% aqueous ammonium hydroxide at 55° C. for 12 hours, cooled, concentrated, and purified by reversed phase HPLC. The DMT-on peak was fractionated, analyzed by capillaiy gel electrophoresis, combined, detritylated, precipitated and lyophilized to a powder.

EXAMPLE 19

Synthesis of fully-modified 5'-[2'-O-methoxyethyl-(GCTGA]-d(TTA-GAG-AGA-G)-[2'-O-methoxyethyl-(GTCCC)-3' phosphorothioate 20-mer <Seq. ID No. 11>.

The synthesis of the above sequence was performed on a Pharmacia OligoPilot II synthesizer on a 180 μmole scale using cyanoethyl phosphoramidite of 2'-deoxyribonucleosides and 2'-O-methoxyethyl substituted ribonucleosides. Pharmacia's HL 30 primer support loaded with 2'-O-methoxyethyl-N4-benzoyl-5-methylcytidine was used. Detritylation was performed using 3% dichloroacetic acid in toluene (volume/volume). Activation of phosphoramidite was done with a 0.22 M solution of pyridinium trifluoroacetate and 0.11 M solution of 1-methylimidazole. Sulfurization was performed using a 0.2 M solution of phenylacetyl disulfide in aceonitrile:3-picoline (1:1 v/v) for 2 minutes. At the end of synthesis, the support was treated with a solution of triethylamine:acetonitrile (1:1, v/v) for 12 hours, support washed with acetonitrile, oligo cleaved, and deprotected with 33% aqueous ammonium hydroxide at 55° C. for 12 hours, cooled, concentrated, and purified by reversed phase HPLC. All DMT fractions were combined, analyzed by capillary gel electrophoresis, detritylated, precipitated and lyophilized to a powder.

EXAMPLE 20

Synthesis of fully modified 5'-[2'-methoxyethyl-(CTG]-d(AGT-CTGTTT)-[2'-methoxyethyl-(TCC-ATT-CT)-3' phosphorothioate 20-mer <Seq. ID No. 12>.

The synthesis of the above sequence was performed on a Pharmacia OligoPilot II synthesizer on a 172 μmole scale using cyanoethyl phosphoramidite of 2'-deoxyribonucleosides and 2'-O-methoxyethyl substituted ribonucleosides. Pharmacia's HL 30 primer support loaded with 2'-O-methoxyethyl-5-methyluridine was used. Detritylation was performed using 3% dichloroacetic acid in toluene (volume/volume). Activation of phosphoramidite was done with a 0.22 M solution of pyridinium trifluoroacetate and 0.11 M solution of 1-methylimidazole. Sulfurization was performed using a 0.2 M solution of phenylacetyl disulfide in aceonitrile:3-picoline (1:1 v/v) for 2 minutes. At the end of synthesis, the support was treated with a solution of triethylamine:acetonitrile (1:1, v/v) for 12 hours, support washed with aceonitrile, oligo cleaved, and deprotected with 33% aqueous ammonium hydroxide at 55° C. for 12 hours, cooled, concentrated, and purified by reversed phase HPLC. All DMT fractions were combined, analyzed by capillary gel electrophoresis, detritylated, precipitated and lyophilized to a powder.

EXAMPLE 21

Synthesis of fully modified 5'-d(GCC-CAA-GCT-GGC)-2'-O-methoxyethyl-(ATC-CGTCA)-3' phosphorothioate 20-mer <Seq. ID No. 14>.

The synthesis of the above sequence was performed on a Milligen 8800 synthesizer on a 282 μmole scale using the cyanoethyl phosphoramidites and Pharmacia's HL 30 primer support. Detritylation was performed using 3% dichloroacetic acid in toluene (volume/volume). Sulfurization was performed using a 0.4 M solution of phenylacetyl disulfide in acetonitrile:3-picoline (1:1 v/v) for 4 minutes. At the end of synthesis, the support was treated with a solution of triethylamine:aceonitrile (1:1, v/v) for 12 hours, support washed with acetonitrile, oligo cleaved, and deprotected with 33% aqueous ammonium hydroxide at 55° C. for 12 hours, cooled, concentrated, and purified by reversed phase HPLC. The DMT-on peak was fractionated, analyzed by capillary gel electrophoresis, combined, detritylated, precipitated and lyophilized to a powder.

EXAMPLE 22

Synthesis of fully-modified 5'-[2'-O-methyl-(TTT-TTT-TTT-TTT-TTT-TTT-TT)-3' phosphorothioate 20-mer <Seq. ID No. 15>.

The synthesis of the above homo-pyrimidine sequence was performed on a Pharmacia OligoPilot II synthesizer on a 180 Emote scale using cyanoethyl phosphoramidite of 5'-O-DMT-2'-O-methyl-5-methyluridine. Pharmacia's HL 30 primer support loaded with 2'-O-methyl-5-methyluridine was used. Detritylation was performed using 3% dichloroacetic acid in toluene (volume/volume). Activation of phosphoramidite was done with a 0.45 M solution of 1H-tetrazole in acetonitrile. Sulfurization was performed using a 0.2 M solution of phenylacetyl disulfide in aceonitrile:3-picoline (1:1 v/v) for 2 minutes. At the end of synthesis, the support was treated with a solution of tiiethylamine:acetonitrile (1:1, v/v) for 12 hours, support washed with acetonitrile, oligo cleaved, and deprotected with 33% aqueous ammonium hydroxide at 55° C. for 12 hours, cooled, concentrated, and purified by reversed phase HPLC. All DMT fractions were combined, analyzed by capillary gel electrophoresis, detritylated, precipitated and lyophilized to a powder.

EXAMPLE 23

Synthesis of fully-modified 5'-[2'-O-methyl-(TTT-TTT-TTT-TTT-TTT-TTT-TT)-3' phosphorothioate 20-mer <Seq. ID No. 15>.

The synthesis of the above homo-pyrimidine sequence was performed on a Pharmacia OligoPilot II synthesizer on a 180 µmole scale using cyanoethyl phosphoramidite of 5'-O-DMT-2'-O-methyl-5-methyluridine. Pharmacia's HL 30 primer support loaded with 2'-O-methyl-5-methyluridine was used. Detritylation was performed using 3% dichloroacetic acid in toluene (volume/volume). Activation of phosphoramidite was done with a0.22 M solution of pyridinium trifluoroacetate and 0.11 M solution of 1-methylimidazole. Sulfurization was performed using a 0.2 M solution of phenylacetyl disulfide in acetonitrile:3-picoline (1:1 v/v) for 2 minutes. At the end of synthesis, the support was treated with a solution of triethylamine:acetonitrile (1:1, v/v) for 12 hours, support washed with acetonitrile, oligo cleaved, and deprotected with 33% aqueous ammonium hydroxide at 55° C. for 12 hours, cooled, concentrated, and purified by reversed phase HPLC. All DMT fractions were combined, analyzed by capillary gel electrophoresis, detritylated, precipitated and lyophilized to a powder.

EXAMPLE 24

Synthesis of fully-modified 5'-[2'-O-methyl-(GCTGA]-d (TTA-GAG-AGA-G)-[2'-O-methyl-(GTCCC)-3' phosphorothioate 20-mer <Seq. ID No. 16>.

The synthesis of the above sequence was performed on a Pharmacia OligoPilot II synthesizer on a 180 µmole scale using cyanoethyl phosphoramidite of 2'-deoxyribonucleosides and 2'-O-methyl substituted ribonucleosides. Pharmacia's HL 30 primer support loaded with 2'-O-methyl-N4-benzoyl-5-methylcytidine was used. Detritylation was performed using 3% dichloroacetic acid in toluene (volume/volume). Activation of phosphoramidite was done with a 0.45 M solution of 1H-tetrazole in acetonitrile. Sulfurization was performed using a 0.2 M solution of phenylacetyl disulfide in aceonitrile:3-picoline (1:1 v/v) for 2 minutes. At the end of synthesis, the support was treated with a solution of triethylamine:acetonitrile (1:1, v/v) for 12 hours, support washed with acetonitrile, oligo cleaved, and deprotected with 33% aqueous ammonium hydroxide at 55° C. for 12 hours, cooled, concentrated, and purified by reversed phase HPLC. All DMT fractions were combined, analyzed by capillary gel electrophoresis, detlitylated, precipitated and lyophilized to a powder. The stepwise sulfurization efficiency was found to 99.5% based on $^{31}$P NMR ($D_2O$).

Those skilled in the art will appreciate that numerous changes and modifications may be made to the preferred embodiments of the invention and that such changes and modifications may be made without departing from the spirit of the invention. It is therefore intended that the appended claims cover all such equivalent variations as fall within the true spilit and scope of the invention.

Various modifications of the invention, in addition to those described herein, will be apparent to those skilled in the art from the foregoing description. Such modifications are intended to fall within the scope of the appended claims.

What is claimed is:

1. A method for the preparation of phosphorothioate oligonucleotides having at least one nucleoside with a 2' modification, said method comprising:

phosphitylating the 5'-hydroxyl of a nucleic acid moiety having at least one nucloeside with a 2' modification in an acetonitrile containing solvent mixture to form a phosphite intermediate; and oxidizing said phosphite intermediate with a substituted acetyl disulfide or acetyl disulfide in an acetonitrile containing solvent mixture for a time sufficient to effect conversion of said phosphite intermediate to said phosphorothioate.

2. The method of claim 1 wherein said oxidizing is in the presence of acetonitrile:lutidine in a ratio of 1:1 based on volume.

3. The method of claim 1 wherein said substituted acetyl disulfide is an arylacetyl disulfide.

4. The method of claim 1 wherein said substituted acetyl disulfide is phenylacetyl disulfide.

5. The method of claim 1 wherein said oxidizing solvent includes pyridine, a sterically hindered pyridine or a blend thereof.

6. The method of claim 5 wherein said sterically hindered pyridine is a collidine, a lutidine or a picoline.

7. The method of claim 1 comprising repeating said phosphitylating and said oxidizing to give said phosphorothioate oligonucleotide having a predetermined length.

8. The method of claim 7 wherein said oligonucleotide comprises from about 6 to about 50 nucleotides.

9. The method of claim 8 wherein said oligonucleotide comprises from about 8 to about 30 nucleotides.

10. The method of claim 1 wherein said phosphite intermediate is a dinucleotide.

11. The method of claim 1 wherein said phosphite intermediate is an oligonucleotide.

12. The method of claim 1 wherein all synthetic steps are performed on an automated synthesizer.

13. The method of claim 12 including using a common solvent during both said phosphitylating and oxidizing steps.

14. The method of claim 12 wherein said acetonitrile containing solvent mixture is used in combination with at least one further solvent in said oxidizing step.

15. The method of claim 1 wherein said phosphitylating is performed using a phosphite moiety.

16. The method of claim 15 wherein said phosphite moiety is a phosphoramidite.

17. The method of claim 1 wherein said phosphitylating step and said oxidizing step are performed in acetonitrile.

18. The method of claim 17 wherein said oxidating step is performed in the presence of a sterically hindered pyridine.

19. The method of claim 18 wherein said pyridine is a picoline.

* * * * *